(12) United States Patent
Küpper

(10) Patent No.: US 6,615,083 B2
(45) Date of Patent: Sep. 2, 2003

(54) IMPLANTABLE MEDICAL DEVICE SYSTEM WITH SENSOR FOR HEMODYNAMIC STABILITY AND METHOD OF USE

(75) Inventor: Bernhard Küpper, Düsseldorf (DE)

(73) Assignee: Medtronic, Inc., Minneapolis, MN (US)

( * ) Notice: Subject to any disclaimer, the term of this patent is extended or adjusted under 35 U.S.C. 154(b) by 331 days.

(21) Appl. No.: 09/842,877

(22) Filed: Apr. 27, 2001

(65) Prior Publication Data

US 2003/0014083 A1 Jan. 16, 2003

(51) Int. Cl.[7] ............................................... A61N 1/365
(52) U.S. Cl. ......................................... 607/25; 600/516
(58) Field of Search ................................. 600/508–509, 600/515–516; 607/1–5, 9, 17, 25

(56) References Cited

U.S. PATENT DOCUMENTS

| | | |
|---|---|---|
| 4,228,803 A | 10/1980 | Rickards |
| 5,228,438 A | 7/1993 | Buchanan |
| 5,330,511 A | 7/1994 | Boute |
| 5,476,487 A | 12/1995 | Sholder |
| 5,507,783 A | 4/1996 | Buchanan |
| 5,514,164 A | 5/1996 | Mann et al. |
| 5,560,370 A | 10/1996 | Verrier et al. |
| 5,772,604 A | 6/1998 | Langberg et al. |
| 5,782,887 A | 7/1998 | van Krieken et al. |
| 6,029,087 A | 2/2000 | Wohlgemuth |

Primary Examiner—Kennedy Schaetzle
Assistant Examiner—Kristen Droesch
(74) Attorney, Agent, or Firm—Thomas F. Woods; Eric R. Waldkoette; Tom G. Berry

(57) ABSTRACT

An implantable medical device system for regulating a heart of a patient. The system includes a first sensor, a second sensor, a processor, and a medical device. The first sensor is capable of sensing activity of a heart atrium. The second sensor is capable of sensing activity of a heart ventricle. The processor is coupled to the first and second sensors and is capable of determining an atrial cycle time and a ventricular cycle time based upon signals from the first and second sensors. The processor is further capable of generating a hemodynamic baseline ratio based upon an atrial cycle time and a ventricular cycle time of a hemodynamic heartbeat, as well as an active ratio based upon an atrial cycle time and a ventricular cycle time of an active heartbeat. The processor is further capable of comparing the hemodynamic baseline ratio and the active ratio, and determining a corrective action based upon this comparison. The medical device is capable of supplying a therapy to the heart and is coupled to the processor. With this configuration, the processor is configured to control desired operation of the medical device based upon the determined corrective action.

70 Claims, 9 Drawing Sheets

IMPLANTABLE MEDICAL DEVICE SYSTEM WITH SENSOR FOR HEMODYNAMIC STABILITY AND METHOD OF USE

FIELD OF THE INVENTION

The present invention relates generally to a system and method used in conjunction with an implantable medical device. More particularly, the present invention relates to a system and method for controlling an implantable medical device based upon sensed information indicative of hemodynamic stability.

BACKGROUND OF THE INVENTION

Cardiac disease affects millions of people throughout the world. Cardiac disease may cause the excitatory and conductive systems of the heart to fail, resulting in an abnormal cardiac rhythm, usually referred to as arrhythmia. Some arrhythmias are very dangerous, and may lead to death of the patient. Other arrhythmias may be the origin of less threatening conditions, but for which medical treatment is nevertheless required. One of the possible treatments for patients suffering from arrhythmia is assistance by an implantable medical device (IMD).

Modern IMDs, such as pacemakers or defibrillators, are complicated electronic devices generally configured to deliver an electrical stimulation to the patient's heart. Alternatively, the IMD can be a drug delivery device, providing controlled distribution of an appropriate drug therapy. Regardless, IMDs are capable of providing assistance on demand, i.e., when the excitatory and conductive systems of the heart fail to operate normally. In order to accommodate specific patient needs, an IMD is normally part of an overall system that constantly monitors heart activity such that the resulting delivered therapy is optimal for the patient.

Overall IMD systems known in the art comprise several components, including the IMD, pacing and/or sensing leads, and a processor. For most applications, the IMD system is pre-programmed to effectuate a desired therapy routine. Often times, it is extremely useful to utilize feedback information from the patient's heart to alter and optimize the therapy routine. To this end, the sensing leads are available for sensing certain cardiac parameters and providing information relating to functioning of the heart, usually on a beat-by-beat basis. The processor analyzes these sensed activities and, based upon appropriate algorithms, determines an optimal therapy, both short-term and long-term. For most pacing applications, two sensing leads are typically provided, one deployed in a heart atrium and the other in a heart ventricle. With this arrangement, an electrocardiogram (ECG) signal is sensed and analyzed. As is well known, the ECG signal provides information indicative of atrial depolarization (P-wave), ventricular depolarization (QRS-wave), and ventricular repolarization (T-wave). Numerous efforts have been made to distinguish the various waves from one another, as well as to classify whether individual wave components indicate heart abnormalities.

For example, previous efforts have been made to utilize ventricular repolarization (ventricular T-wave) information to control a rate response, AV delay, and to predict arrhythmias. Examples of such applications are provided in Table 1 below:

TABLE 1

| U.S. Pat. No. | Inventor(s) | Issue Date |
|---|---|---|
| 5,560,370 | Verrier et al. | Oct. 1, 1996 |
| 5,330,511 | Boute | Jul. 19, 1994 |
| 4,228,803 | Rickards | Oct. 21, 1980 |

All patents listed in Table 1 are hereby incorporated by reference herein in their respective entireties. As those of ordinary skill in the art will appreciate readily upon reading the Summary of the Invention, Detailed Description of the Preferred Embodiments, and claims set forth below, many of the devices and methods disclosed in the patents of Table 1 may be modified advantageously by using the teachings of the present invention.

Noticeably absent from prior cardiac sensing and analyzing systems is information relating to atrial repolarization (atrial T-wave or atrial PT-wave). Due to the relatively small electrical activity associated with atrial repolarization and because atrial repolarization occurs during the predominant ventricular depolarization, it has previously been assumed that atrial repolarization is impossible to sense, as evidenced by the patents listed in Table 2.

TABLE 2

| U.S. Pat. No. | Inventor(s) | Issue Date |
|---|---|---|
| 5,772,604 | Langberg et al. | Jun. 20, 1998 |
| 5,514,164 | Mann et al. | May 07, 1996 |
| 5,507,783 | Buchanan | Apr. 16, 1996 |
| 5,476,487 | Shoulder | Dec. 19, 1995 |
| 5,228,438 | Buchanan | Jul. 20, 1993 |

All patents listed in Table 2 above are hereby incorporated by reference herein in their respective entireties. As those of ordinary skill in the art will appreciate readily upon reading the Summary of the Invention, Detailed Description of the Preferred Embodiments, and claims set forth below, many of the devices and methods disclosed in the patents of Table 2 may be modified advantageously by using the teachings of the present invention.

More recently, the ability to sense atrial repolarization has become possible. In particular, the advent of digital signal processing (DSP) has provided a tool that can be employed to effectively sense atrial repolarization. In this regard, Wolgemuth, U.S. Pat. No. 6,029,087, issued Feb. 22, 2000, the teachings of which are incorporated herein by reference, describes in detail DSP solution for sensing, processing, and classifying intracardiac signals so as to provide the IMD with reliable cardiac event data via DSP technology. Through the event classification based upon DSP information described by Wolgemuth, atrial repolarization, and thus total atrial cycle time for a heartbeat can now be sensed.

One disadvantage of prior art systems, including those listed in Tables 1 and 2 above, relates to the inability to utilize atrial repolarization information in controlling and/or optimally setting a specific IMD implanted in a specific patient. Therefore, there is a continuing need for a system and method that evaluates cardiac functioning utilizing atrial repolarization information for optimizing IMD therapy.

SUMMARY OF THE INVENTION

The present invention overcomes the disadvantages of the prior art by providing a method of, and a system for, controlling an IMD based upon atrial cycle time, including atrial repolarization, information.

The present invention has certain objects. That is, the present invention provides solutions to certain problems existing in the prior art such as: (a) an inability to utilize the atrial repolarization portion of a cardiac signal to evaluate functioning of a heart; (b) an inability to utilize the atrial repolarization portion of a cardiac signal to control an implantable medical device; (c) an inability to predict short-term deviations from a hemodynamic situation; (d) an inability to control an implantable medical device to correct short-term deviations from a hemodynamic situation; (e) an inability to predict long-term deviations from a hemodynamic situation; (f) an inability to control an implantable medical device to correct long-term deviations from a hemodynamic situation; (g) an inability to evaluate heart operation based upon a correlation between atrial cycle time, including atrial repolarization, relative to ventricular cycle time; (h) an inability to control an implantable medical device based upon a correlation between atrial cycle time, including atrial repolarization, relative to ventricular cycle time.

The system and method of the present invention provides certain advantages including: (a) the ability to utilize the atrial repolarization portion of a cardiac signal to evaluate functioning of a heart; (b) the ability to utilize the atrial repolarization portion of a cardiac signal to control an implantable medical device; (c) the ability to predict short-term deviations from a hemodynamic situation; (d) the ability to control an implantable medical device to correct short-term deviations from a hemodynamic situation; (e) the ability to predict long-term deviations from a hemodynamic situation; (f) the ability to control an implantable medical device to correct long-term deviations from a hemodynamic situation; (g) the ability to evaluate heart operation based upon a correlation between atrial cycle time, including atrial repolarization, relative to ventricular cycle time; (h) the ability to control an implantable medical device based upon a correlation between atrial cycle time, including atrial repolarization, relative to ventricular cycle time.

The system and method of the present invention has certain features, including sensing atrial cycle time and ventricular cycle time for a particular heartbeat. The atrial cycle time includes the atrial repolarization period. A hemodynamic baseline ratio is generated based upon the atrial cycle time and the ventricular cycle time of an electrical heartbeat representing the hemodynamical cycle time of a heartbeat. Also, an active ratio is generated based upon an atrial cycle time and a ventricular cycle time of an active heartbeat. By comparing the hemodynamic baseline ratio and the active ratio, a corrective action can be determined. In this regard, a medical device is controlled to effectuate the determined corrective action. Essentially, then, electrical signals provided by the heart are sensed and then linked or correlated to a hemodynamical situation that results from the electromechanical coupling in each chamber of the heart.

DESCRIPTION OF THE PREFERRED EMBODIMENTS

Figure 1:
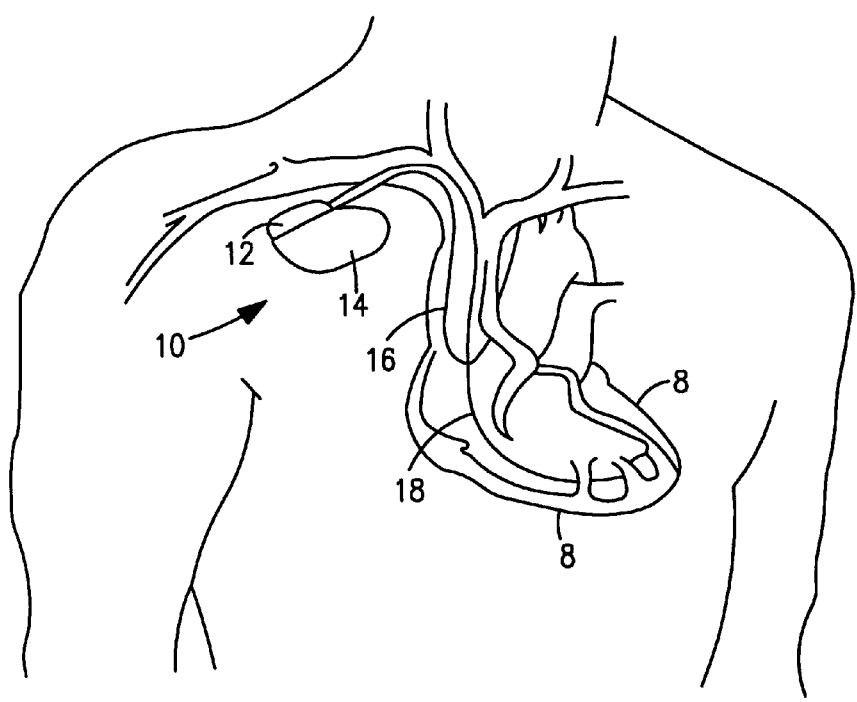
FIG. 1 is a simplified schematic view of one embodiment of an implantable medical device.

FIG. 1 is a simplified schematic view of one embodiment of implantable medical device ("IMD") 10 forming part of an implantable medical device system in accordance with the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
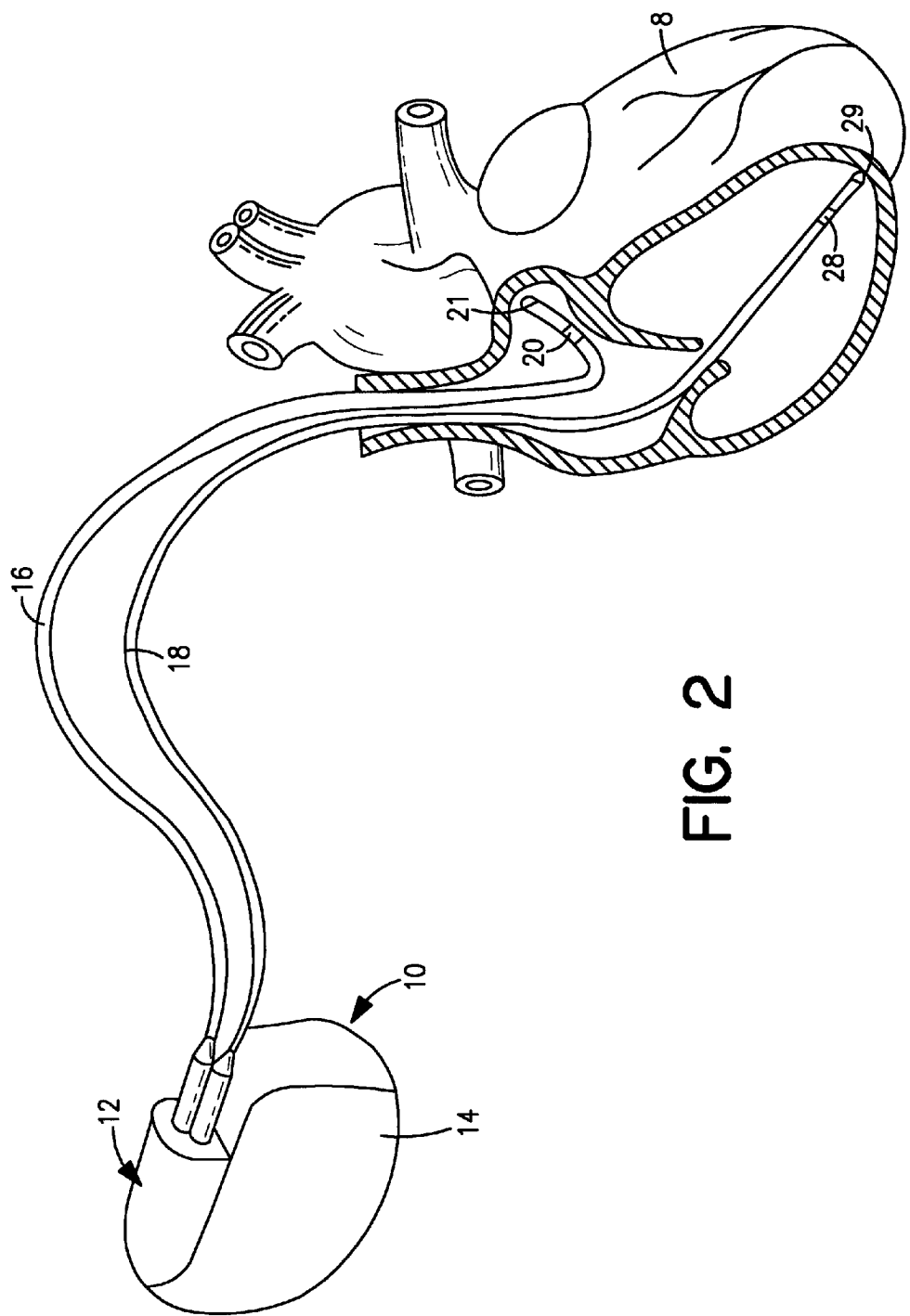
FIG. 2 is a simplified illustration of an implantable medical device with leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle. The leads 16, 18 can be tissue connected leads, floating leads, or a combination of tissue connected leads and floating leads.

Figure 3:
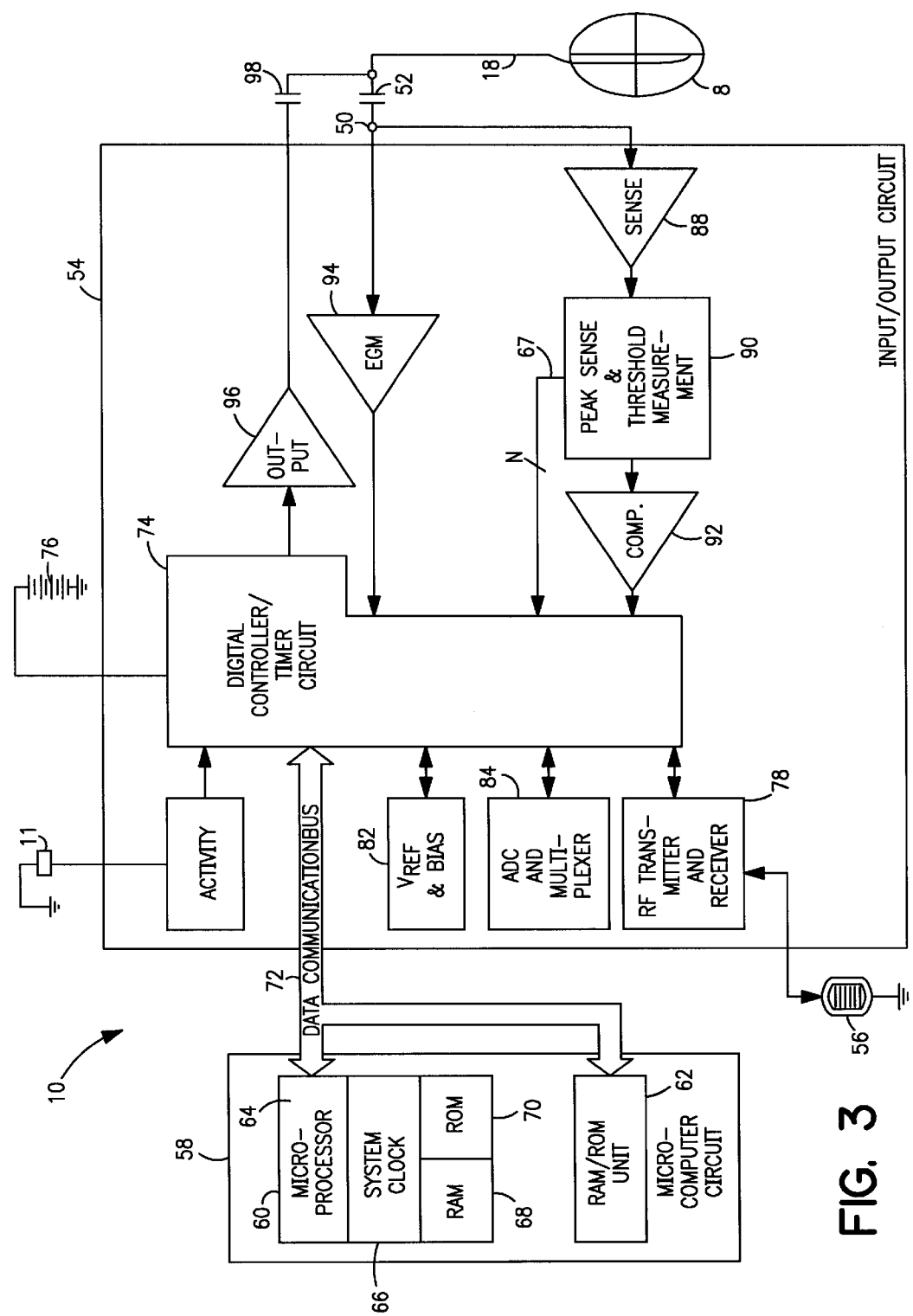
FIG. 3 is a block diagram illustrating the constituent components of an implantable medical device.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components. In addition, microcomputer circuit 58 (or input/output circuit 54) preferably incorporates digital signal processing (DSP) technology, such as that described in U.S. Pat. No. 6,029,087 to Wolgemuth, the teachings of which are incorporated herein by reference.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8. More particularly, and as described in greater detail below, the sensed electrogram signal can be analyzed, via DSP technology, to determine atrial depolarization, atrial repolarization, ventricular depolarization, and ventricular repolarization.

In some preferred embodiments of the present invention, IMD 10 may operate in various non-rate-responsive modes, including, but not limited to, DDD, DDI, VVI, VOO and VVT modes. In other preferred embodiments of the present invention, ID 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
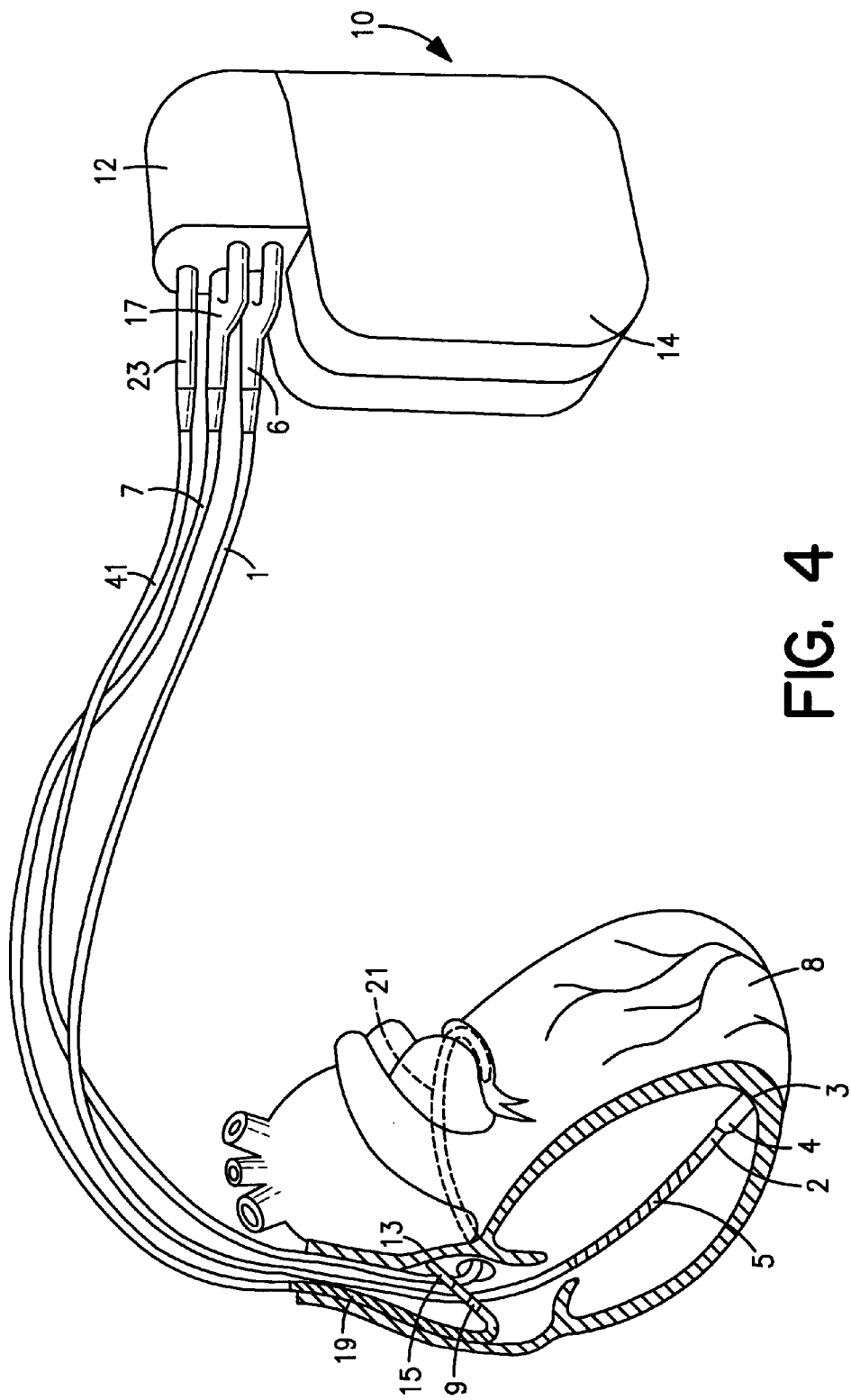
FIG. 4 is a simplified schematic view of an implantable medical device with leads positioned within passageways of a heart.
Figure 5:
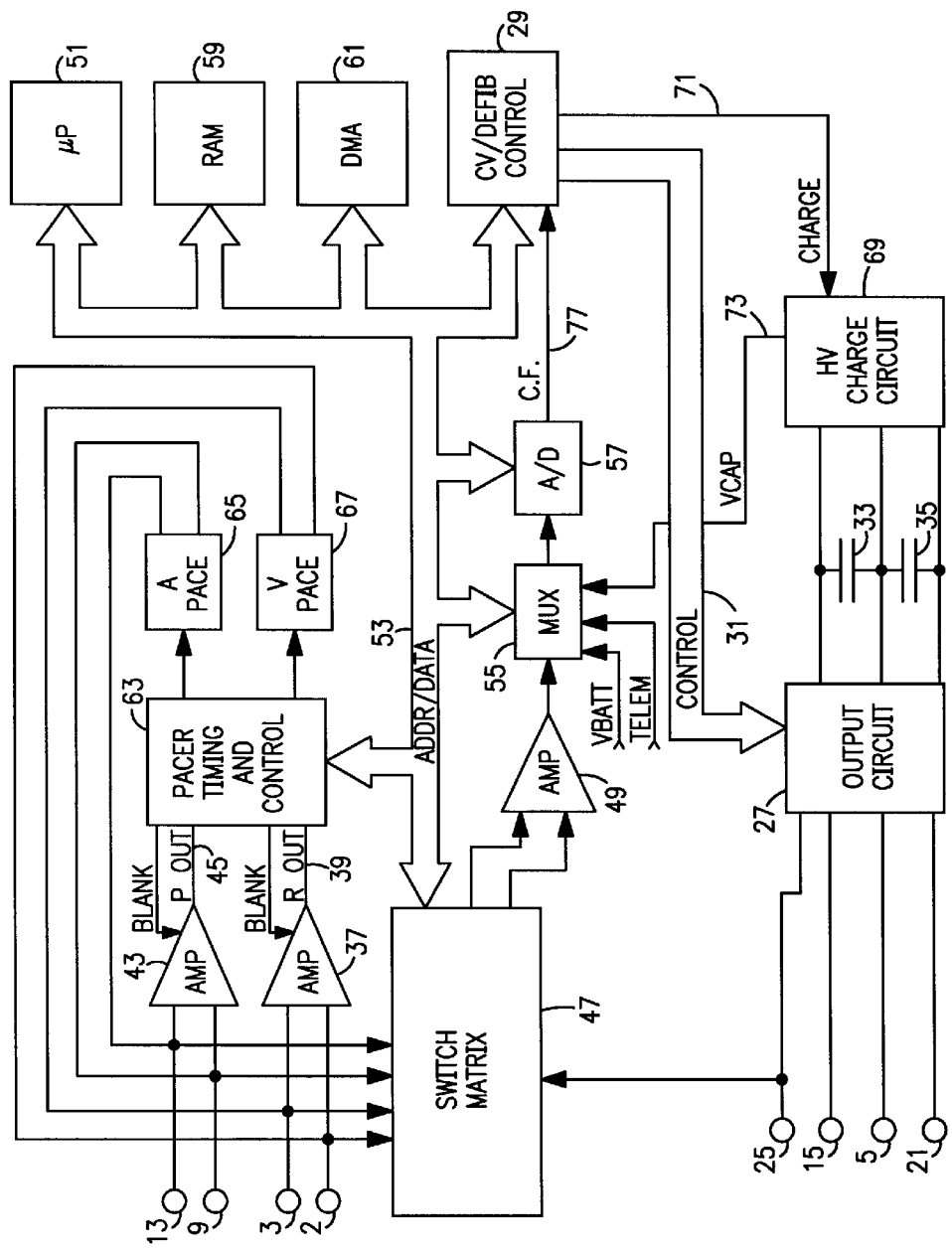
FIG. 5 is a partial block diagram illustrating one embodiment of an implantable medical device used in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 that carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5-200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts. In addition, microprocessor 51 is capable of determining atrial repolarization (PT-wave) and ventricular repolarization (RT-wave or QT-wave).

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No.

5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry that may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. Even further, IMD 10 can be a drug delivery system, as known in the art. The present invention is believed to find wide application to any form of implantable heart therapy device for use in conjunction with electrical leads.

Figure 6:
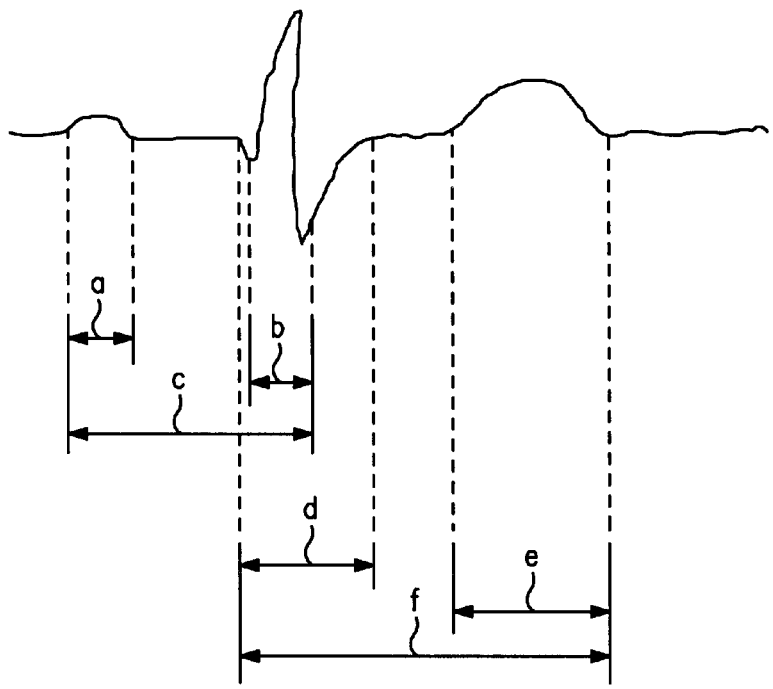
FIG. 6 is an example of an enlarged electrocardiogram from a patient in a normal sinus rhythm.

The system and method of the present invention utilizes atrial cycle time to evaluate heart activity and determine appropriate corrective actions and/or therapies. In this regard FIG. 6 illustrates a typical surface electrocardiogram (ECG) wave form for a normal sinus rhythm or heartbeat and is characterized by a P-wave, corresponding with atrial depolarization and contraction of the atria, followed by the QRS complex (QRS-wave or R-wave) that corresponds generally with depolarization and contraction of the ventricles. A T-wave follows the QRS complex and corresponds with ventricular repolarization.

With the availability of DSP, it is now possible to effectively sense the atrial repolarization period, otherwise "hidden" within the QRS complex. FIG. 6 illustrates the initiation and termination of each depolarization and repolarization event during a cardiac cycle relative to the ECG waveform. Notably, while FIG. 6 relates to a surface ECG wave, the system and method of the present invention will preferably utilize intracardial signals to ascertain various components of the cardiac cycle. As is well known, these intracardial signals appear quite different from a surface ECG wave. However, the surface ECG wave conveniently illustrates the various cardiac cycle components being acted upon by the system and method of the present invention, such that FIG. 6 is provided to most clearly describe the present invention.

With the above explanation in mind, the time period of atrial depolarization (or P-wave) is illustrated as "a", whereas the time period of atrial repolarization (PT-wave) is designated at "b". Taken in combination, the total atrial cycle time is denoted as "c", and reflects the time period from initiation of atrial depolarization a to termination of atrial repolarization b. Similarly, the ventricular depolarization period (QRS-wave or R-wave) is designated as "d", whereas the ventricular repolarization period (T-wave or QT-wave) is designated as "e". Taken in combination, the total ventricular cycle time is designated as "f", and represents a time period from initiation of ventricular depolarization d to termination of ventricular repolarization e.

With the above designations in mind, the system and method of the present invention makes use of a correlation between total atrial cycle time c and total ventricular cycle time f to evaluate functioning of a patient's heart. In particular, and in a preferred embodiment, a processor, such as the microcomputer circuit 58 previously described with respect to FIG. 3, determines a ratio of atrial cycle time/ventricular cycle time, and then compares the ratio or resulting value relative to a hemodynamic baseline ratio or value. In general terms, the sensed and determined ratio will, according to the Frank-Starling Law remains stable so long as the heart remains in a stable situation. A change in the sensed ratio relative to the hemodynamic baseline ratio is indicative of abnormal cardiac activity.

Figure 7:
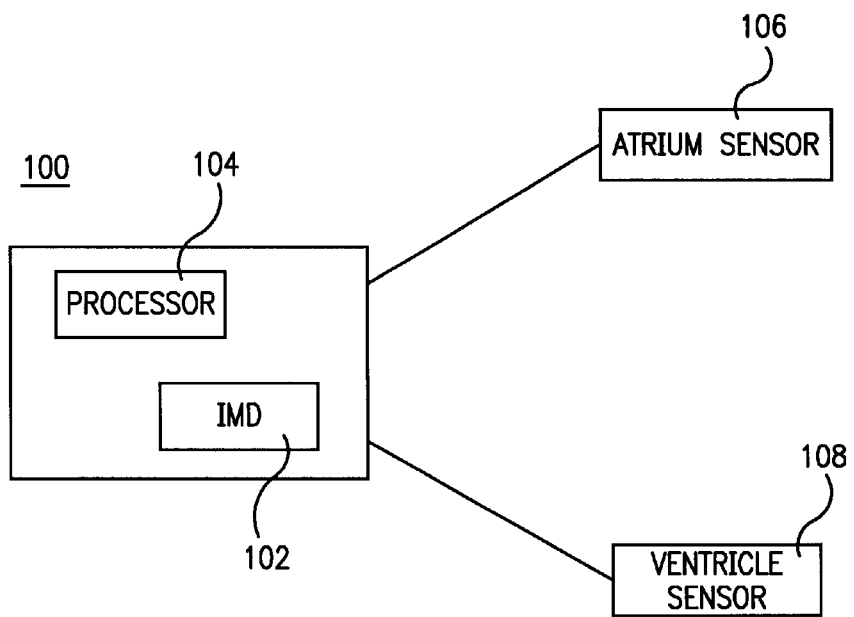
FIG. 7 is a block diagram of an implantable medical device system in accordance with the present invention.

With the above in mind, FIG. 7 illustrates in block form an IMD system 100 in accordance with the present invention. The system 100 includes an IMD 102, a processor 104, an atrium sensor 106, and a ventricle sensor 108. The IMD 102 can assume any of the forms previously described, such as a pacemaker, defibrillator, drug delivery system, etc. In one preferred embodiment, the IMD 102 is a dual chamber pacemaker. Similarly, the processor 104 can assume any of the forms previously described, and is preferably a microprocessor incorporating DSP technology. Finally, the atrium sensor 106 and the ventricle sensor 108 are also of types known in the art and previously described. In a preferred embodiment, the sensors 106, 108 are capable of sensing activity of a heart atrium and a heart ventricle, respectively. Taken in combination, the processor 104 is electrically coupled to the sensors 106, 108, and is configured to control the IMD 102. In a preferred embodiment, at least one of the sensors 106, 108 is a QT sensor available from Medtronic, Inc. The processor 104 is capable of determining an atrial cycle time and a ventricular cycle time based upon signals from the atrium sensor 106 and the ventricle sensor 108. As described in greater detail below, the processor 104 is further capable of generating a hemodynamic baseline ratio based upon an atrial cycle time and a ventricular cycle time of a hemodynamic heartbeat, as well as generating an active ratio based upon an atrial cycle time and a ventricular cycle time of an active heartbeat. The processor 104 is further capable of comparing the hemodynamic baseline ratio and the active ratio, and determining a necessary corrective action based upon this comparison. Finally, the processor 104 is capable of prompting and controlling the IMD 102 to effectuate the determined corrective action.

Figure 8:
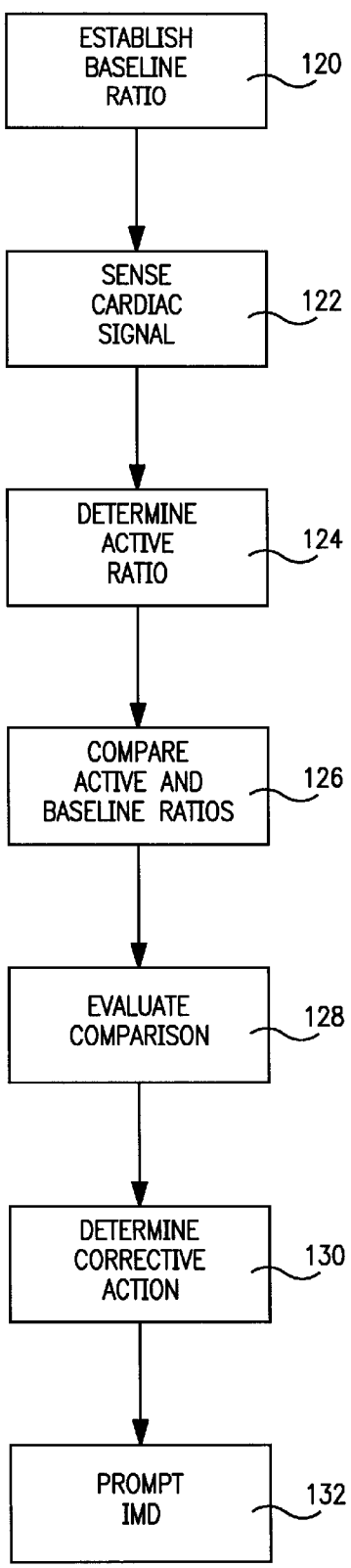
FIG. 8 is a flow chart illustrating a method of controlling an IMD in accordance with the present invention.

With further reference to the flow diagram of FIG. 8, operation of the system 100 begins at step 120 at which a hemodynamic baseline ratio is established. In a preferred embodiment, the hemodynamic baseline ratio is calculated according to the following equation:

$$\frac{\text{Atrial Cycle Time for Hemodynamic Heartbeat}}{\text{Ventricular Cycle Time for Hemodynamic Heartbeat}}$$

The hemodynamic baseline ratio can be a predetermined value programmed by a user into the processor 104. Alternatively, as described in greater detail below, the processor 104 can establish the hemodynamic baseline ratio by analyzing a series of heartbeats.

Regardless of how the hemodynamic baseline ratio is established, at step 122, a cardiac signal associated with a patient's heartbeat is sensed via the sensors 106, 108. For purposes of clarification, and as used throughout the specification, reference to an "active heartbeat" relates to a particular heartbeat monitored by the system 100 following establishment of the hemodynamic baseline ratio. That is to say, heartbeats (or "preliminary heartbeats") may be sensed and analyzed to arrive at the hemodynamic baseline ratio. Once established, however, the system continuously monitors subsequent or "active" heartbeats, and processes the information accordingly.

At step 124, the processor 104 determines an active ratio, preferably according to the following equation:

$$\frac{\text{Atrial Cycle Time for Active Heartbeat}}{\text{Ventricular Cycle Time for Active Heartbeat}}$$

Once again, the atrial cycle time includes both atrial depolarization time period and atrial repolarization time period for the active heartbeat. The ventricular cycle time includes the ventricular depolarization period and the ventricular repolarization period for the active heartbeat.

The processor 104 then compares the active ratio to the hemodynamic baseline ratio at step 126. The processor 104 evaluates the implications of the comparison at step 128. To this end, the processor 104 preferably includes software having one or more algorithms configured to analyze the comparison between the hemodynamic baseline ratio and the active ratio. For example, in accordance with the Frank-Starling Law, an impairment between the atrial and the ventricular wall tension will be reflected in a deviation of the active ratio from the hemodynamic baseline ratio. Depending upon the magnitude and direction of the deviation (i.e., positive or negative), the algorithm will determine or predict the onset of an arrhythmia, as well as the likely cause, such as too long or too short AV conduction time or a ventricular iscaemia, frequency, tension of the muscular walls, myocardiatis, myocardium infarction, indocarditis, etc.

In response to the evaluation of step 128, the processor 104 then determines a corrective action at step 130. Again, the algorithm associated with the processor 104 generates a technical input that is used to determine an appropriate change, if necessary, in therapy being provided by the IMD 102. For example, where the IMD 102 is a pacemaker, the determined corrective action can be a change in the AV delay, lower rate limit, upper rate limit, preventative pacing, night rate drop, etc. Alternatively, where the IMD 102 is a drug delivery system, the corrective action can be an increase or decrease in drug dispersion frequency and/or volume. Regardless, at step 132, the processor 104 prompts the IMD 102 to effectuate the determined corrective action.

Figure 9:
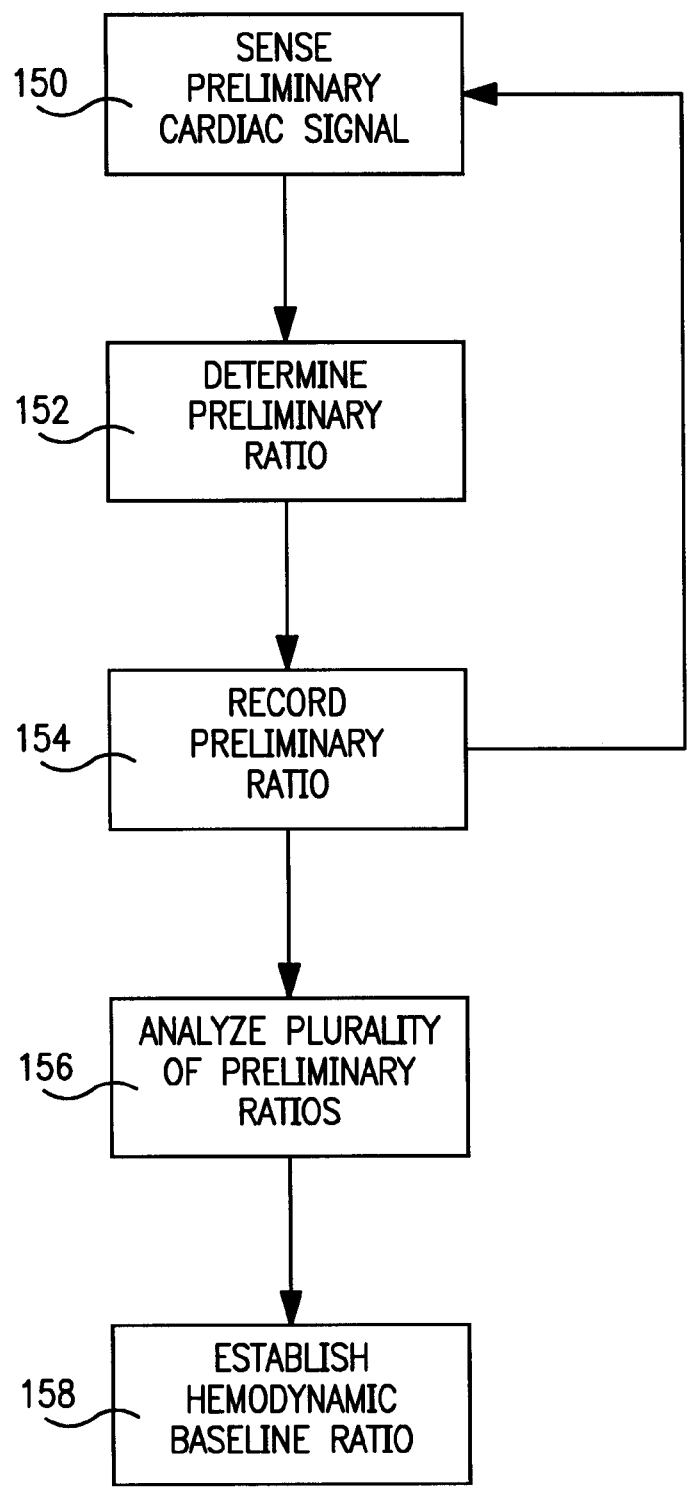
FIG. 9 is a flow chart illustrating establishing a hemodynamic baseline ratio in accordance with the present invention.

As previously described, the hemodynamic baseline ratio can be predetermined or can be generated by the system 100. For example, FIG. 9 provides a flow diagram illustrating one method of generating the hemodynamic baseline ratio. Beginning at step 150, a cardiac signal for a preliminary heartbeat is sensed. Once again, a "preliminary heartbeat" is relative to use of the system 100 prior to establishing the hemodynamic baseline ratio. At step 152, a preliminary ratio is determined for the preliminary heartbeat based upon the sensed signal. The preliminary ratio is preferably determined as follows:

$$\frac{\text{Atrial Cycle Time for Preliminary Heartbeat}}{\text{Ventricular Cycle Time for Preliminary Heartbeat}}$$

Again, the atrial cycle time includes atrial depolarization and atrial repolarization time periods for a preliminary heartbeat, whereas the ventricular cycle time includes ventricular depolarization and ventricular repolarization time periods for a preliminary heartbeat. At step 154, the determined preliminary ratio is recorded within a memory of the processor 104.

As shown in FIG. 9, the same steps are repeated to generate plurality of preliminary ratios. At step 156, the plurality of preliminary ratios are correlated with one another, preferably via an appropriate algorithm. In this regard, other factors potentially influencing one or more of the preliminary ratios are accounted for to compensate for deviations in the variously recorded ratios. Effectively, the plurality of preliminary ratios serves as a learning period for the system 100. Finally, at step 158, the hemodynamic baseline ratio is established based upon the above-described analysis. Notably, once the hemodynamic baseline ratio has been established, the system 100 operates as a closed loop regulation circuit.

In addition to reacting to short-term deviations from a hemodynamic situation, the system and method of the present invention is preferably also configured to detect and compensate for long-term variations. In particular, the system can record a series of active ratios and/or comparative results (relative to the hemodynamic baseline ratio) over an extended period of time and then use a trend analysis to evaluate long-term cardiac inefficiencies. For example, an individual active ratio may deviate only slightly from the hemodynamic baseline ratio, such that the algorithm does not dictate a change in therapy. However, over time the trend analysis may establish that the atrial cycle time and ventricular cycle time are slowly changing (e.g., shortening), but at slightly different rates. The system and method of the present invention analyzes this long-term information to evaluate the propriety of the selected therapy routine. Alternatively or in addition, the same information can be provided to the patient's physician who performs his/her or own analyses. Regardless, based upon this long-term data relating to a plurality of active ratios, the particular therapy is then modified to optimize heart performance. Along these same lines, the system and method of the present invention can utilize long-term trend analysis to better estimate the destabilization process of the patient's heart. For example, the trend analysis may indicate that the atrial cycle time and the ventricular cycle time are both decreasing, but not at equal rates. In this case, the absolute deviation between a particular active ratio and the hemodynamic baseline ratio is less significant so that no short-term therapy modifications are required. However, the algorithms associated with the system and method of the present invention can correlate the long-term trend information and generate a multiplication factor to either the sensed atrial cycle time or the sensed ventricular cycle time to eliminate a medium-fast bias otherwise affecting faster changes in heart destabilization.

Yet another analysis technique made available with the system and method of the present invention is the ability to confirm the sufficiency of other parameters intended to optimize the hemodynamic performance of the heart. For example, the comparison of an active ratio with the hemodynamic baseline ratio for a particular heartbeat can be compared with other functions of the IMD (e.g., automatic AV-delay optimization, iscaemia detection, etc.), and then evaluate whether those other parameters are functioning as desired. Even further, the long-term trend analysis is available to indicate the necessity of other therapy compensations. For example, a continuous search for the hemodynamical optimal lower rate limit (LRL) can be guided by the active ratio, as the lowest LRL will exhibit the longest atrial cycle time and ventricular cycle time that still provides a stable active ratio. A graphical illustration of this analysis is provided in FIGS. 10A and 10B. In particular, FIG. 10A graphically illustrates data from a heartbeat designated as being hemodynamically stable. In particular, sensed portions of the hemodynamically stabile heartbeat of FIG. 10A exhibits an atrial cycle time ($X_1$) accorded a value of "2", and a ventricular cycle time ($Y_1$) accorded a value of a "2.4". The resulting hemodynamic baseline ratio, in accordance with one preferred correlation technique is thus 0.833 (i.e., 2/2.4).

Figure 10A:
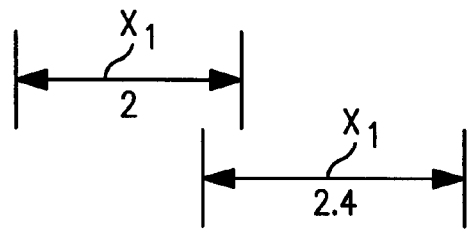
FIGS. 10A–10D are illustrative results of cardiac signal analyses performed in accordance with the present invention.
Figure 10B:
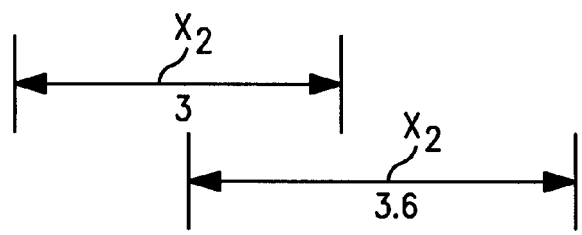

FIG. 10B illustrates the optimal lower rate limit associated with the same patient, as determined by the system and method of the present invention, in which the sensed cardiac cycle has an atrial cycle time ($X_2$) of "3", and a ventricular cycle time ($Y_2$) of "3.6". The resulting ratio active of 0.833 (i.e., 3/3.6) is deemed to be hemodynamically stable, as it does not deviate from the hemodynamic baseline ratio previously described with respect to FIG. 10A. The system and method of the present invention, however, is able to identify this hemodynamically stable situation, in conjunction with the longest atrial cycle time and ventricular cycle time, and thus designate these times as the optimal LRL.

Figure 10C:
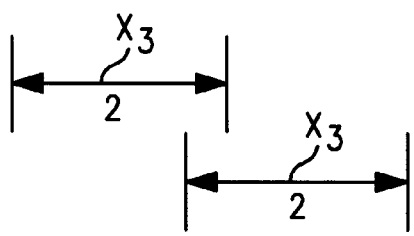

To further exemplify operation of the system and method of the present invention, FIG. 10C relates to the same patient as analyzed in FIG. 10A, and graphically illustrates a subsequently sensed cardiac signal. In particular, for the active signal analyzed by FIG. 10C, the atrial cycle time ($X_2$) is accorded a value of "2", and the ventricular cycle time ($Y_2$) is accorded a value of "2". The resulting active ratio is 1.0 (i.e., 2/2). A comparison of the active ratio of 1.0 to the hemodynamic baseline ratio of 0.833 causes the system and method of the present invention, via an internal algorithm, to identify the cardiac signal associated with the graph of FIG. 10C as being unstable. In particular, the active ratio of 1.0 is greater than the hemodynamic baseline ratio, with the system and method designating this instability as being an unstable ventricular activity. In this instance, the algorithm may call for a rise frequency corrective action.

Figure 10D:
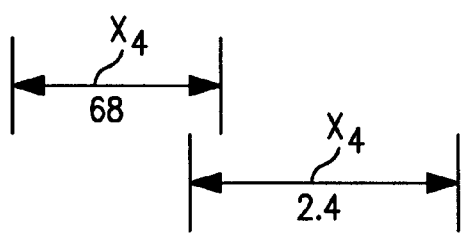

A further exemplary analysis provided by the system and method of the present invention is graphically illustrated in FIG. 10D. Once again, the graph of FIG. 10D relates to a cardiac signal of the patient for which the hemodynamic baseline ratio of FIG. 10A was previously established. With respect to FIG. 10D, a sensed active cardiac signal has been determined to have an atrial cycle time ($X_2$) value of "1.8", and a ventricular cycle time ($Y_4$) value of "2.4". The resulting active ratio is 0.075 (i.e., 1.8/2.4). A comparison of this active ratio with the hemodynamic baseline ratio (0.833) reveals an unstable situation. In particular, a decrease of the active ratio relative to the hemodynamic baseline ratio indicates unstable atrial hemodynamics. As a result, the system and method of the present invention, may, via an internal algorithm, identify an AV/delay corrective action, for example.

The system and method of the present invention provides a marked improvement over previous implantable medical device system designs. In particular, by utilizing atrial cycle time, including atrial repolarization time, the system and method of the present invention provides a unique approach to atrial and ventricular management. Both short-term and long-term atrial or ventricular instabilities relative to hemodynamic functioning are consistently identified by the system and method of the present invention, and appropriate corrective action is provided.

In the claims section of this application, means-plus-function clauses are intended to cover the structures described herein as performing the recited function and not only structural equivalents but also equivalent structures. For example, although a nail and a screw may not be structurally equivalent in that a nail employs a cylindrical surface to secure wooden parts together, whereas a screw employs a helical surface, in the environment of fastening wood parts, a nail and a screw are equivalent structures.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims. For example, while the preferred correlation between utilized to evaluate deviation from a hemodynamically stable situation has preferably been described as being the ratio of atrial cycle time/ventricular cycle time. Other correlations are also available. For example, the applied correlation can be a ratio of ventricular cycle time/atrial cycle time; atrial repolarization period/ventricular repolarization period; ventricular repolarization period/atrial repolarization period; atrial depolarization period/atrial repolarization period; ventricular depolarization period/ventricular repolarization period; etc.

What is claimed:

1. A system for evaluating functioning of a heart of a patient in conjunction with an implantable medical device, the system comprising:
   a first sensor capable of sensing activity of a heart atrium;
   a second sensor capable of sensing activity of a heart ventricle; and
   a processor coupled to the first and second sensors, the processor configured for:
      determining an atrial cycle time and a ventricular cycle time for a heartbeat based upon signals from the first and second sensors,
      generating an active ratio based upon atrial cycle time and ventricular cycle time of an active heartbeat,
      comparing the active ratio to a hemodynamic baseline ratio,
      evaluating functioning of the heart based upon the comparison.

2. The system of claim 1, wherein the processor is further capable of establishing the hemodynamic baseline ratio based upon an atrial cycle time and a ventricular cycle time of a hemodynamic heartbeat.

3. The system of claim 2, wherein the processor is capable of analyzing a plurality of preliminary ratios, each based upon an atrial cycle time and a ventricular cycle time of a respective preliminary heartbeat, to establish the hemodynamic baseline ratio.

4. The system of claim 1, wherein the active ratio is atrial cycle time/ventricular cycle time for the active heartbeat.

5. The system of claim 1, wherein the processor is capable of determining an atrial depolarization period and an atrial repolarization period for the active heartbeat.

6. The system of claim 1, wherein the processor is capable of determining a ventricular depolarization period and a ventricular repolarization period for the active heartbeat.

7. The system of claim 1, wherein the processor is capable of determining a corrective therapy for the patient based upon the comparison of the active ratio and the hemodynamic baseline ratio.

8. The system of claim 1, wherein the processor is capable of generating a trend based upon a plurality of active ratios in comparison to the hemodynamic baseline ratio, and evaluating functioning of the heart based upon the trend.

9. An implantable medical device system for regulating a heart of a patient, the system comprising:
 a first sensor capable of sensing activity of a heart atrium;
 a second sensor capable of sensing activity of a heart ventricle;
 a processor coupled to the first and second sensors, the processor configured for:
  determining an atrial cycle time and a ventricular cycle time based upon signals from the first and second sensors,
  generating a hemodynamic baseline ratio based upon an atrial cycle time and a ventricular cycle time of a hemodynamic heartbeat,
  generating an active ratio based upon an atrial cycle time and a ventricular cycle time of an active heart beat,
  comparing the hemodynamic baseline ratio and the active ratio,
  determining a corrective action based upon the comparison of the hemodynamic baseline ratio and the active ratio; and
 a medical device capable of delivering a therapy to the patient and coupled to the processor;
 wherein the processor is configured to prompt desired activation of the medical device based upon the determined corrective action.

10. The system of claim 9, wherein the medical device is a pacemaker.

11. The system of claim 10, wherein the pacemaker is a dual chamber pacemaker.

12. The system of claim 11, wherein the dual chamber pacemaker contains the processor.

13. The system of claim 9, wherein the medical device is a defibrillator.

14. The system of claim 9, wherein the medical device is a drug delivery system.

15. The system of claim 9, wherein the first sensor is a PT sensor.

16. The system of claim 9, wherein the second sensor is a QT sensor.

17. The system of claim 9, wherein the processor is a microprocessor.

18. The system of claim 9, wherein the hemodynamic baseline ratio is a ratio of atrial cycle time/ventricular cycle time of a hemodynamic heartbeat.

19. The system of claim 9, wherein the active ratio is a ratio of atrial cycle time/ventricular cycle time of an active heartbeat.

20. The system of claim 9, wherein the processor is capable of determining an atrial repolarization period, the atrial repolarization period being part of the atrial cycle time.

21. The system of claim 20, wherein the processor is further capable of determining an atrial depolarization period, the atrial depolarization period being part of the atrial cycle time.

22. The system of claim 9, wherein the processor is capable of determining a ventricular depolarization period, the ventricular depolarization period being part of the ventricular cycle time.

23. The system of claim 22, wherein the processor is capable of determining a ventricular repolarization period, the ventricular repolarization period being part of the ventricular cycle time.

24. The system of claim 9, wherein the processor is configured to perform digital signal processing.

25. The system of claim 9, wherein the processor is capable of predicting an arrhythmia based upon the comparison of the hemodynamic baseline ratio and the active ratio.

26. The system of claim 9, wherein the processor includes an algorithm for operating upon the comparison of the hemodynamic baseline ratio and the active ratio.

27. The system of claim 9, wherein the processor is capable of recording a plurality of active ratios each based upon atrial cycle times and ventricular cycle times of a plurality of heartbeats, respectively.

28. The system of claim 27, wherein the processor is capable of establishing an active ratio trend based upon the plurality of active ratios.

29. The system of claim 28, wherein the processor is capable of comparing the active ratio trend with the hemodynamic baseline ratio and determining a corresponding corrective action.

30. An implantable medical device system for regulating a heart of a patient, the system comprising:
 first sensing means for sensing an atrial cycle time of a heartbeat;
 second sensing means for sensing a ventricular cycle time of a heartbeat;
 processing means for generating an active ratio based upon the sensed atrial cycle time and the sensed ventricular cycle time of an active heartbeat;
 comparing means for comparing the active ratio to a hemodynamic baseline ratio;
 analyzing means for determining a corrective action based upon a comparison of the active ratio and the hemodynamic baseline ratio; and
 heart therapy means for delivering a therapy to the patient based upon the determined corrective action.

31. The system of claim 30, wherein the heart therapy means comprises means for delivering electrical stimulation to the patient.

32. The system of claim 30, wherein the heart therapy means comprises means for delivering a drug to the patient.

33. The system of claim 30, wherein the first sensing means includes means for sensing an atrial repolarization period of a heartbeat.

34. The system of claim 33, wherein the first sensing means includes means for sensing an atrial depolarization period of a heartbeat.

35. The system of claim 34, wherein the first sensing means includes a PT sensor.

36. The system of claim 30, wherein the second sensing means includes means for sensing a ventricular depolarization period of a heartbeat.

37. The system of claim 36, wherein the second sensing means includes means for sensing a ventricular repolarization period of a heartbeat.

38. The system of claim 37, wherein the second sensing means includes a QT sensor.

39. The system of claim 30, wherein the first sensing means and the second sensing means include digital signal processing means.

40. The system of claim 30, wherein the analyzing means includes a microprocessor and an algorithm for evaluating the comparison of the active ratio and the hemodynamic baseline ratio.

41. The system of claim 38, further comprising:
determining means for determining the hemodynamic baseline ratio.

42. The system of claim 41, wherein the determining means includes means for establishing an atrial cycle time and a ventricular cycle time of a hemodynamic heartbeat.

43. The system of claim 42, wherein the determining means processes information from the first and second sensing means to determine the hemodynamic baseline ratio.

44. The system of claim 43, wherein the determining means includes means for analyzing a plurality of preliminary ratios each based upon a preliminary atrial cycle time and a preliminary ventricular cycle time for respective preliminary heartbeats.

45. The system of claim 30, wherein the active ratio is sensed atrial cycle time/sensed ventricular cycle time.

46. The system of claim 30, further comprising:
recording means for recording a plurality of active ratios.

47. The system of claim 46, further comprising:
correlating means for correlating the plurality of active ratios in comparison to the hemodynamic baseline ratio.

48. A method for applying therapy with an implantable medical device to a heart of a patient, the method comprising:
sensing an atrial cycle time for a first heartbeat;
sensing a ventricular cycle time for the first heartbeat;
generating an active ratio for the first heartbeat based upon the sensed atrial cycle time and the sensed ventricular cycle time;
comparing the active ratio to a hemodynamic baseline ratio;
determining a corrective action based upon the comparison; and
applying a therapy to the heart to effectuate the determined corrective action.

49. The method of claim 48, wherein sensing an atrial cycle time includes sensing an atrial repolarization period for the first heartbeat.

50. The method of claim 49, wherein sensing the atrial repolarization period includes digitizing an ECG signal for the first heartbeat.

51. The method of claim 49, wherein sensing the atrial cycle time further includes sensing an atrial depolarization period for the first heartbeat.

52. The method of claim 51, wherein sensing the atrial cycle time includes determining a time period from initiation of the atrial depolarization period to termination of the atrial repolarization period.

53. The method of claim 48, wherein sensing a ventricular cycle time includes sensing a ventricular depolarization period for the first heartbeat.

54. The method of claim 53, wherein sensing a ventricular cycle time further includes sensing a ventricular repolarization period for the first heartbeat.

55. The method of claim 54, wherein sensing the ventricular cycle time includes determining a time period from initiation of the ventricular depolarization period to termination of the ventricular repolarization period.

56. The method of claim 48, wherein generating an active ratio includes determining a ratio of atrial cycle time/ventricular cycle time for the first heartbeat.

57. The method of claim 48, further comprising:
establishing the hemodynamic baseline ratio.

58. The method of claim 57, wherein establishing the hemodynamic baseline ratio includes:
determining an atrial cycle time for a hemodynamic heartbeat; and
determining a ventricular cycle time for a hemodynamic heartbeat.

59. The method of claim 58, wherein determining an atrial cycle time for a hemodynamic heartbeat includes determining an atrial repolarization period for a hemodynamic heartbeat.

60. The method of claim 58, wherein establishing the hemodynamic baseline ratio further includes:
determining a ratio of atrial cycle time/ventricular cycle time for a hemodynamic heartbeat.

61. The method of claim 58, wherein establishing the hemodynamic baseline ratio further includes:
monitoring a plurality of preliminary heartbeats;
determining an atrial cycle time for each of the preliminary heartbeats;
determining a ventricular cycle time for each of the preliminary heartbeats;
determining a preliminary ratio for each of the preliminary heartbeats, wherein each preliminary ratio is based upon the respective atrial and ventricular cycle times of the preliminary heartbeats; and
correlating the preliminary ratios to establish the hemodynamic baseline ratio.

62. The method of claim 57, wherein the hemodynamic baseline ratio is a predetermined value.

63. The method of claim 48, wherein comparing the active ratio to the hemodynamic baseline ratio includes identifying an instability in an atrium of the patient.

64. The method of claim 48, wherein comparing the active ratio to a hemodynamic baseline ratio includes identifying an instability in a ventricle of the patient.

65. The method of claim 48, wherein comparing the active ratio to the hemodynamic baseline ratio includes identifying onset of an arrhythmia.

66. The method of claim 48, further comprising determining a plurality of active ratios based upon atrial cycle time and ventricular cycle time for a plurality of heartbeats, respectively.

67. The method of claim 66, further comprising formulating an activity trend for the heart based upon the plurality of active ratios.

68. The method of claim 67, further comprising determining an optimal lower rate limit for the heart based upon the activity trend.

69. The method of claim 48, wherein applying a therapy to the heart includes delivering an electrical stimulation to the patient.

70. The method of claim 48, wherein applying a therapy to the heart includes delivering a drug to the patient.

* * * * *

UNITED STATES PATENT AND TRADEMARK OFFICE
CERTIFICATE OF CORRECTION

PATENT NO. : 6,615,083 B2
DATED : September 2, 2003
INVENTOR(S) : Bernhard Kupper It is certified that error appears in the above-identified patent and that said Letters Patent is hereby corrected as shown below:

<u>Column 16,</u>
Line 56, delete "processor configured for;" and insert -- processor capable of --.

Signed and Sealed this

Thirtieth Day of May, 2006

JON W. DUDAS
*Director of the United States Patent and Trademark Office*